United States Patent [19]

Irwin

[11] Plant 4,422

[45] May 29, 1979

[54] KALANCHOE PLANT

[75] Inventor: Lawrence T. Irwin, Canyon, Tex.

[73] Assignee: J & L Plants Inc., Canyon, Tex.

[21] Appl. No.: 922,514

[22] Filed: Jul. 7, 1978

[51] Int. Cl.[2] ..... A01H 5/00
[52] U.S. Cl. ..... Plt./68
[58] Field of Search ..... Plt./68

*Primary Examiner*—Robert E. Bagwill

*Assistant Examiner*—James R. Feyrer
*Attorney, Agent, or Firm*—Frank B. Robb

[57] ABSTRACT

There is disclosed a Kalanchoe Plant having a tall habit of 16 to 20 inches, flowers borne on stems well above the foliage, vivid, bright red color of blooms with moderate yellowish pink tones, ability to maintain flower color and form in dark environments, and non-closing habit at night.

1 Drawing Figure

DESCRIPTION OF THE INVENTION

My present invention relates to a new and distinct variety of Kalanchoe Plant which I have selected from a large number of other plants being grown by me and whose parentage comprises the Kalanchoe Plant known as "Exotic" (U.S. Plant Pat. No. 3,149), and "Ramona" an unpatented variety which combination has produced several varieties which have distinct and differing characteristics with some common and desirable characteristics maintained likewise, all being grown for commercial production.

In accordance with my planned program of breeding, and using the parent plant "Exotic" and crossing the same with "Ramona" the unpatented variety, I have been able to produce plants which have many desirable characteristics, including those of the instant plant variety which is one having a highly branched habit with sturdy upright characteristics, and which are maintained in the various plants produced therefrom, with consistent results with the commercial production being carried on in greenhouses in Canyon, Tex.

The instant variety is distinguished among others and from the parent variety and from other varieties of which I am aware as evidenced by the unique combination of principal characteristics which are outstanding in the new variety and which make it a valuable addition to the various kalanchoe varieties that are presently being produced by me and are commercially available in the trade, among those characteristics in the varieties which I previously developed being the following:

(1) Highly branched sturdy upright habit with plant height of 16 to 20 inches;

(2) The profuse blooming habit;

(3) Flowers borne on stems 6 inches above foliage;

(4) The earliness to bloom;

(5) Vivid bright red color of blooms with moderate yellowish pink tones;

(6) The retention of flower color and form in dark environments;

(7) A non-closing habit at night.

Reproduction by me of the plant asexually, by means of cuttings in my program of breeding and commercial production presently being carried out and continuously performed by me in my greenhouse located in Canyon, Tex., discloses that the foregoing characteristics and distinctions come true, are established, and are transmitted through succeeding propagations.

Among the particularly distinguishing and distinct aspects of my plant are the tall plant height, 16 to 20 inches, the fact that a single cutting will produce a very desirable commercial plant as contrasted with other plants which require at least three cuttings, the bright red color of blooms with many of them having moderate yellowish pink tones and earliness to bloom.

Perhaps the two most outstanding characteristics of this particular variety which I have chosen to designate as #53, are the aspects of retention of flower color and form in dark environments such as may often be encountered in the home, and the non-closing habit at night, a very unusual aspect not common in this variety at all.

In the accompanying drawing I have shown the flowers of a typical blooming plant of my new variety in closeup view, and depicted in colors which are as nearly true as is possible to make the same in a color illustration of this character, always bearing in mind that the colors designated hereinafter, are those made by comparison with a plant under normal greenhouse lighting conditions and in fiberglas greenhouses, these being uniformly observed throughout my program and references made thereto accordingly.

There follows a description of my new variety, with color terminology where applicable in accordance with comparisons made with the Munsell Color Cascade, published by Macbeth Division of Kollmorgen Corporation, except where general color terms which have ordinary dictionary significance are applicable and appropriate.

Parentage: Seedling.
Seed parent: "Exotic" (Plant Pat. No. 3,149).
Pollen parent: "Ramona" (unpatented).
Propagation: Holds its distinguishing characteristics through succeeding propagation by cuttings.
Locality where grown and observed: Canyon, Tex.
Plant:

*Form.*—Tall; much branched; upright; averaging 16 to 20 inches in height.

*Growth habit.*—Medium; upright; branching.

*Rooting habit.*—Coordinate; any part of the stem will form a fibrous root system and it roots easily from such part.

*Blooming habit.*—Natural flowering occurs approximately December 15, the plant being a short day plant.

*Blooming season.*—It can be brought into bloom year around by appropriate photoperiodic manipulation including day length manipulation.

Foliage:

*Size.*—Large.

*Quantity.*—Abundant.

*Color.*—New foliage — Upper side — (21-15); under side of leaves — (21-14). Old foliage — upper side of leaves — (20-15); Under side of leaves — (20-14).

*Shape.*—Obtuse; oval.

*Texture.*—Upper side — glossy and smooth; under side — smooth.

*Edge of margin.*—Crenate. Shape — oval. Aspect — obtuse.

Disease resistance: Side by side comparison with other varieties in my greenhouse, indicate that it is much more disease resistant than older standard varieties grown in the same greenhouse under the same conditions at Canyon, Tex.

Flower: Pistillate; staminate.

*Size.*—Flower diameter — 1.6 cm; Flower depth — 1.5 cm; Petal width — 6 mm; Petal length — 8 mm.

*Form.*—Umbel.

*Color.*—Petals — upper side — (37-12); lower side — (35-2).

*Blooming period.*—4 to 5 weeks.

Hardiness: When grown in my greenhouse, no problems seem to be noticeable in a range of 50 degrees F. to 100 degrees F.

General observations: This particular variety has all the characteristics of a good pot plant, its vigor, vivid bright red color and upright form make it distinctive from other kalanchoes. The ability to flower in 12 weeks and avail of a single cutting to make a large pot plant make it particularly commercially desirable.

SUMMARY

It is notable that the particular variety hereof, is distinguished from the other varieties which were developed from the same parentage, and are the subject of other United States patent applications, in that the color is distinctive, the vivid bright red thereof being quite attractive, the fact that the colors of the flowers will be maintained in dark home-type environments and that the flowers do not close at night in dark environments, make it particularly further distinctive.

It shares some of the same characteristics with other kalanchoe plants, which have common parentage, including the tall upright vigorous aspect, the ability to flower early, 10 days before its parent "Ramona", the medium to large size, flexible foliage of fern green color, flowers carried on the stem 6 inches above the foliage and year around flowering effected by photoperiodic manipulation.

I claim:

1. A new and distinct variety of Kalanchoe Plant, substantially as herein shown and described, characterized particularly as to novelty by the unique combination of a tall, 16 to 20 inch habit, flowers borne on stems 6 inches above the foliage, earliness to bloom, vivid, bright red color of blooms with moderate yellowish pink tones, retention of flower color and form in dark environments, and non-closing habit at night.

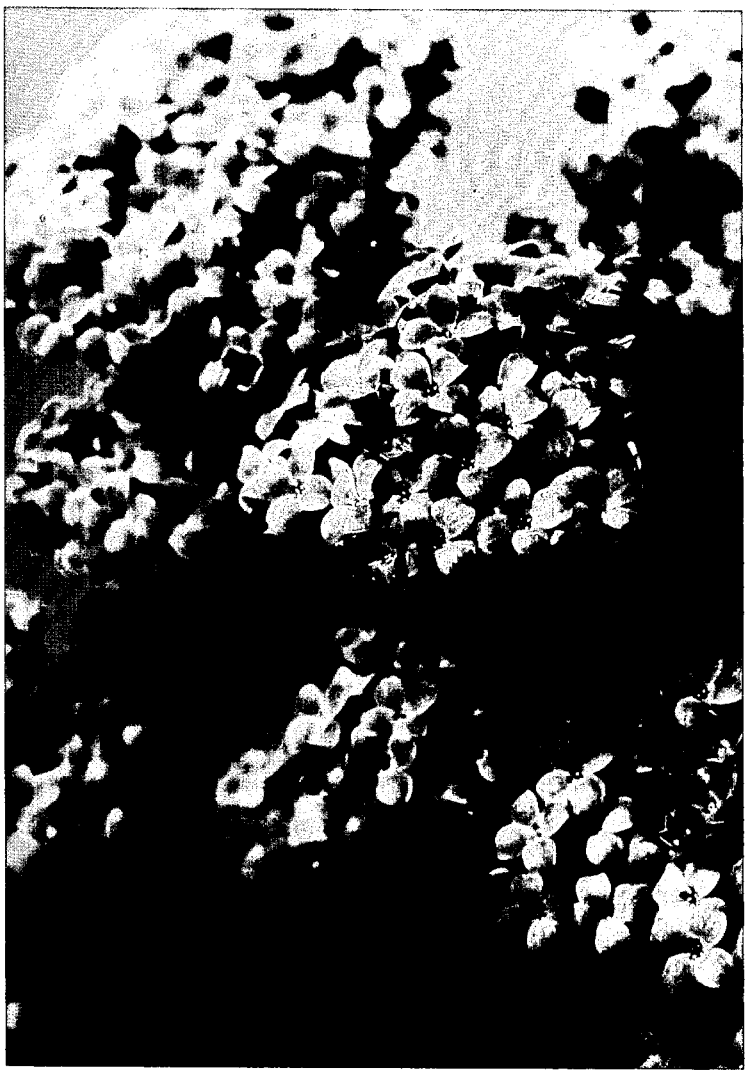

* * * * *